United States Patent
Wegner

(10) Patent No.: US 6,815,408 B2
(45) Date of Patent: Nov. 9, 2004

(54) HYDROGEN PEROXIDE STABILIZER AND RESULTING PRODUCT AND APPLICATIONS

(76) Inventor: Paul C. Wegner, 1340 Eaton Ave., San Carlos, CA (US) 94070

( * ) Notice: Subject to any disclaimer, the term of this patent is extended or adjusted under 35 U.S.C. 154(b) by 86 days.

(21) Appl. No.: 10/359,942

(22) Filed: Feb. 6, 2003

(65) Prior Publication Data

US 2003/0151024 A1 Aug. 14, 2003

Related U.S. Application Data

(60) Provisional application No. 60/355,601, filed on Feb. 11, 2002.

(51) Int. Cl.[7] .......................... C11D 17/04; C11D 3/00; D06L 17/04
(52) U.S. Cl. ...................................... 510/278; 510/372
(58) Field of Search ................. 510/278, 372

(56) References Cited

U.S. PATENT DOCUMENTS

| | | | |
|---|---|---|---|
| 4,414,305 A | * | 11/1983 | Nakamura et al. .......... 430/373 |
| 4,469,780 A | * | 9/1984 | Hirai et al. .................. 430/373 |
| 4,592,892 A | | 6/1986 | Ueno et al. |
| 4,880,725 A | * | 11/1989 | Hirai et al. .................. 430/373 |
| 5,118,436 A | * | 6/1992 | Aoyagi et al. ......... 252/186.42 |
| 5,270,033 A | | 12/1993 | Montgomery |
| 5,437,868 A | | 8/1995 | Oakes et al. |
| 5,489,434 A | | 2/1996 | Oakes et al. |
| 5,695,913 A | * | 12/1997 | Nakamura et al. .......... 430/373 |
| 5,718,910 A | | 2/1998 | Oakes et al. |
| 5,888,483 A | * | 3/1999 | Pahlck et al. .................. 424/61 |
| 5,891,087 A | * | 4/1999 | Ohtani et al. .................. 604/89 |
| 6,348,187 B1 | | 2/2002 | Pan et al. |
| 6,352,821 B1 | * | 3/2002 | Makuta et al. .............. 430/405 |
| 6,468,472 B1 | | 10/2002 | Yu et al. |
| 6,689,798 B2 | * | 2/2004 | Shimada et al. ............ 514/333 |

* cited by examiner

Primary Examiner—Yogendra N. Gupta
Assistant Examiner—John M. Petruncio
(74) Attorney, Agent, or Firm—Frank J. Benasutti

(57) ABSTRACT

Hydrogen peroxide is stabilized by the addition of tri-potassium phosphate. This enhanced product is environmentally friendly and can be used in a variety of odor and disinfection applications without hazard to people, plants and things.

2 Claims, No Drawings

HYDROGEN PEROXIDE STABILIZER AND RESULTING PRODUCT AND APPLICATIONS

CROSS-REFERENCE TO RELATED APPLICATION

This application is a Continuation-in Part of my prior co-pending application, entitled HYDROGEN PEROXIDE STABILIZER, Ser. No. 60/355,601, field Feb. 11, 2002; the disclosure of which is incorporated herein by reference as if fully set forth.

BACKGROUND OF THE INVENTION

1. Technical Field

This invention relates to hydrogen peroxide and, more particularly, to providing an alkaline and stable mixture of aqueous hydrogen peroxide; and to the uses of this enhanced product.

2. Background Art

Hydrogen peroxide is a known bleaching agent. In general, it is sold as in solution with water, that is, it is an aqueous solution. As I use the term hydrogen peroxide hereinafter, I mean the aqueous solution. Normally, hydrogen peroxide decomposes into oxygen and water. In the prior art, an acidic material, such as phosphoric acid, is added to the solution to extend its shelf life. Hydrogen peroxide is typically stabilized with phosphoric acid and/or acetanilide. Acetanilide decomposes under alkaline conditions to form materials which can catalytically decompose hydrogen peroxide. It is desirable to have a mixture which maximizes the bleaching speed (oxidation speed) of the hydrogen peroxide, while minimizing its rate of decomposition. Usually bleaching speed is increased at the expense of increased decomposition rate. Bleaching speed and decomposition rate usually increase as the pH increases. Therefore, it is desirable to have an additive which buffers at a high pH and acts as an effective stabilizer without compromising its oxidation speed. In addition, it is desirable to have an active agent whose oxidation power is just short of being able to bleach common dyes used to color fabric or destroy the fabric itself, but strong enough to bleach common stains such as food and drink. Generally, as the pH increases and the oxidation power increases, the ability to disinfect articles also increases. A common example is sodium hypochlorite, which is very alkaline and a strong oxidizer. Many odors can be reduced or eliminated with oxidation agents, but they are destructive to fibers, impart an unpleasant odor, and are toxic to the environment.

DISCLOSURE OF THE INVENTION

Summary of the Invention

I have invented a product comprising hydrogen peroxide and tri-potassium phosphate.

The product of my invention consists of three components: hydrogen peroxide; water as a diluent; and an alkaline phosphate, pyrophosphate, or polyphosphate salt. The salt acts as a stabilizer and accelerator. In accordance with my invention, I want to maximize oxidation.

Also, additional agents or conditioners can be added to increase its oxidation speed.

Further, I have invented uses for this product, which are environmentally friendly, such as use as a bleaching agent, an odor control agent, and a disinfectant. It can be applied for odor control and disinfection to an air handling system by introducing a product comprising hydrogen peroxide and tri-potassium phosphate into the intake of the air handling system.

DESCRIPTION OF THE PREFERRED EMBODIMENTS

The product consists of three components: hydrogen peroxide; water as a diluent; and an alkaline phosphate, pyrophosphate, or polyphosphate salt. The salt acts as a stabilizer and accelerator. Additional agents or conditioners can be added to increase its oxidation speed.

It is preferred that all the components be free or have low concentrations of materials which can contribute to the decomposition of hydrogen peroxide, such as organic matter, transition metals, and other material.

The most preferred salt is tri-potassium phosphate. It provides a high level of stabilization to the hydrogen peroxide, while maintaining reasonable oxidation activity (bleaching action).

Pharmaceutical grade hydrogen peroxide (3.5% hydrogen peroxide to water by weight) yields the most stable activated hydrogen peroxide. The best formulation is: tri-potassium phosphate at 1 to 10 grams per liter of 3.5% hydrogen peroxide. Four grams per liter is the most preferred. Higher concentrations of both components can be used, but the mixture becomes progressively more unstable.

Typically, distilled water is mixed with tri-potassium phosphate. Hydrogen peroxide 35% is added to the resulting solution. One part hydrogen peroxide to 9 parts water is preferred. The product can be used directly or diluted with distilled or with de-ionized water. Alternately, to maximize storage life, the product can be packaged as two separate components of stabilized hydrogen peroxide and water containing tri-potassium phosphate. These two components can be mixed prior to use, or applied sequentially.

Additional agents can be added to the product to enhance its oxidation speed. Once applied, the product can be exposed to light or heat to accelerate the oxidation speed. These agents are favored because they can be employed at the point of application and do not add chemicals to the product; which means increased storage life and less chemical residue. The best way to enhance effectiveness of the product is by simple evaporation after application. The hydrogen peroxide concentration increases along with its activity, with minimal decomposition.

In terms of chemical accelerators, potassium hydroxide is the material of choice. It increases oxidation speed of the product the most with the least amount of decomposition. These accelerators can be combined with the product, or applied at the point of use.

Other useful accelerators are potassium carbonate, sodium hydroxide, sodium carbonate, ammonium hydroxide, and ethanol amine.

Product Compositions

In general, hydrogen peroxide concentration required for odor control and disinfection is lower than that required for bleaching out stains. A hydrogen peroxide concentration of 0.1% up to 8% is sufficient for many applications, without being corrosive or difficult to transport and store. High concentrations are useful, but less safe to handle.

The tri-potassium phosphate (stabilizer-accelerator) is added at a level sufficient to promote adequate stabilization and activity. A level of 100 PPM to 2,000 PPM for a hydrogen peroxide of about 4% is sufficient. Concentrations may be modified individually for other applications.

Chemical accelerators should be added in amounts just sufficient to achieve the desired oxidation speed. This amount could be 10 times higher than the stabilizer-accelerator.

The water, stabilizer-accelerator, and optional chemical accelerator should be combined first, followed by the slow addition of the hydrogen peroxide. Cold and dark mixing and storage conditions are favored.

Potassium saturated fatty acid salts can be added to enhance the degreasing properties of the agent without harming the stability of the activated hydrogen peroxide.

The tri-potassium phosphate can be added to the hydrogen peroxide as a dry powder to produce the activated hydrogen peroxide. It is more convenient to ship the dry powder.

Less preferred salts are: dipotassium phosphate, tetra potassium pyrophosphate, potassium polyphosphate, disodium phosphate trisodium phosphate, tetra sodium pyrophosphate, sodium polyphosphate, diammonium phosphate, tri-ammonium phosphate, tetra ammonium pyrophostate, and ammonium polyphosphate. These are functional, but less acceptable due to reduced stabilization, oxidation speed, odor acceptability, or taste acceptability. These phosphate salts can also be formed in situ by reacting alkaline materials such as potassium hydroxide with the phosphoric acid stabilizer that is present in some stabilized hydrogen peroxide sources. Sodium salts can be toxic to some plants.

Alternately, a concentrated form of hydrogen peroxide 35% to 90% can be diluted with pure water or with pure water containing the phosphate salt stabilizer.

Distilled water or de-ionized water is the preferred diluent.

Methods of Application

In many cases, the product can be applied as a spray or fine aerosol. It is most effective when applied and allowed to dry at room temperature. The product becomes more active as the water evaporates and hydrogen peroxide becomes more concentrated. In many cases, no rinsing is necessary because of the low solid residue. In some cases, the totally dissolved solids (TDS) level meets potable water standards. In addition, no organic soap residues are introduced; which could act as food sources for odor causing bacteria, decompose into odiferous materials, or cause subsequent dirt to stick to the article being cleaned.

The product is mild enough to be introduced into ventilation, air conditioning, and heating systems of airplanes, trains, cars, buses, and buildings, while people are occupying these areas; to disinfect and deodorize the air and system itself.

The product can be applied as a liquid to articles such as textiles, paper pulp, hair bleach and dye, as a tooth bleach, for mouthwash, water disinfection, wash water, pools, saunas, and spas.

The application of light or heat accelerates the action of the product. These methods of acceleration are preferred over the addition of chemical accelerators, because they can be easily introduced at the time of application and do not add to the residue level. The addition of chemical accelerators such as potassium hydroxide should be added close to the time of use to maximize the shelf life of the hydrogen peroxide. Chemical accelerators generally increase the activity of the hydrogen peroxide at the expense of increased hydrogen peroxide loss from decomposition into oxygen gas.

Specific Applications

Dry Cleaning, Carpet and Upholstery Cleaning

The product is best applied as a pretreatment to carpets. In some cases, applying and allowing to dry is a sufficient procedure. The addition of chemicals may be desirable to accelerate the speed of the agent. The product has the benefits of being odorless, colorless, non-foaming, and disinfecting. It also removes stains, odors, dirt and oils without damaging the carpet or leaving a significant residue. After the pretreatment, the carpet is preferably washed with distilled or deionized water. The water is removed from the carpet with a vacuum device such as a carpet extractor. This further reduces the level of residues in the carpet.

Food, Agricultural Products, and Food Contact Disinfection and Deodorization

In many cases, it is desirable to disinfect food and food contact areas without affecting the taste of the food being handled. Presently, chlorine-based bleaches, such a chlorine, bromine, and iodine based products are the accepted disinfection agents. All these materials can impart a bad taste, are toxic, can produce toxic chemicals, or otherwise render the food products unacceptable. Examples of these areas are dairies, bottling plants, canneries, meat processing, agricultural product washing, food processing plants, and restaurants. The product can be applied to these areas to reduce odor and increase the level of sanitation without the risk of toxicity or imparting a bad taste to the items, due to product residues. It can also be applied to a food item itself.

Dental, Medical, Child Care, Geriatric Facilities, Hair and Nail Salons

Odor control and sanitation control are a chronic problem in these areas. The product is applied as needed with minimal risk of toxicity or damage to materials, while providing odor control and disinfection activity. The product is mild enough to apply to the skin, hair, and mouth areas without irritation or unpleasant taste. It eliminates the unpleasant odors; and bleaches or disinfects without being toxic. The concentration of the product would depend on the application. Many hair dyes and bleaches contain nitrogen-based accelerators that are irritating, have an unpleasant odor that is toxic, or cause damage to the areas of contact. Many skin cleansers contain materials that are considered toxic. This product is nontoxic and mild.

The agent can be used for cow teat and hand disinfection.

Plant Disinfection

Many plants are sensitive to the elements of chlorine, bromine, iodine, sodium, and boron. Those elements make them an unacceptable form of insect and disease control. This product contains only potassium phosphate and hydrogen peroxide (which decompose into oxygen and water). All of these materials are considered essential for the growth of plants. Therefore, any remaining residue can be used by the plant. In addition, tri-potassium phosphate acts as an excellent wetting agent to insure thorough contact with the plant. This wetting action also kills many insects.

Drinking Water Disinfection

In some cases, it is desirable to disinfect water without imparting an unpleasant taste, in such applications as drinking water for bottling operations, and remote site water disinfection. The product is useful in this application.

The agent will remove chlorine odor and taste from water and surfaces.

Odor and Sanitation Control of Enclosed Areas

In many cases, it is desirable to remove odors and disinfect areas occupied by people or animals, such as hotels, cars, buses, airplanes, trains, hospitals, restaurants, restrooms, theaters, health spas, swimming pool areas, kennels, pet stores, cat litter boxes, and the like. The application of chlorine or ozone can be impractical in the presence of people, due to their unpleasant odor and toxicity.

My product can be used without these disadvantages. Odors may include smoke, skunk, mildew, mold, urine, fecal matter, decomposing organic matter, body odor, and other unpleasant odors. In some case, microbes may have colonized air conditioning systems or heating systems that have been allowed to remain cool during the warmer months of the year. These odors can be particularly apparent when the furnace is first turned on after several months of being idle. These odors can be greatly reduced by introducing a fine spray of the product into the furnace or air conditioning (i.e., heating, ventilating and air conditioning duct) intake when the furnace is turned on. Air conditional odors can be reduced by introducing a fine spray of the product while the unit is running.

Laundry, Dry Cleaning, Textiles, Paper Pulp

The product can be applied as a spray or liquid. The treated material can be exposed to evaporative conditions, heat, or light to accelerate the rate of bleaching (stain removal). In general, evaporation in the presence of light yields the best results for a given amount of hydrogen peroxide. In cases where only odor removal is required, or minimal moisture is allowable, such as dry cleaning, higher concentrations of hydrogen peroxide and an application as a fine aerosol is preferred.

Dealing with Applications Where Unpleasant Odors are Strong

Portable toilets, toilets, restrooms, cat litter boxes, dead animal areas, decaying organic matter, sewers, dumpsters, morgues, cleaning and food processing equipment, waste processing equipment, and oil processing equipment can benefit from application of my product. In these cases, where immediate odor elimination is the desired result, the product is applied as a spray or fine aerosol. Odor knockdown is rapid.

Positive Attributes of My Product

Removes stains;

Deodorizes;

Disinfects;

Useful in mold and mildew abatement;

Kills some insects;

Emulsifies to help remove oils and greases;

Removes dirt;

A mild bleach that is color safe towards many fabric dyes;

Odorless and does not create unpleasant odors when applied;

Colorless and clear;

Leaves no organic (soap, perfume, enzyme) residue;

Leaves only trace amounts of inorganic residue;

No perfumes;

Non-foaming;

Mild taste;

Does not impart an unpleasant taste to many foods and agricultural products;

Does not damage most materials;

Environmentally friendly, since it decomposes into plant food and water;

Can be applied as an aerosol in the presence of people and animals;

Good buffering at high pH;

Nontoxic to plants and animals; and

Good stability.

In addition, it provides the following benefits, at the concentration in which it is applied:

Buffering action at high pH to ensure high oxidation activity;

Odorless;

Colorless;

Clear;

Acceptable taste at the concentrations in which it is applied;

Oil and grease emulsifier;

Non-foaming properties;

Dirt removing properties; and

Low toxicity to animals, plants, and the environment.

Post Treatment of Articles to Maintain Odor and Microbial Control

My hydrogen peroxide product is a useful "point of use" disinfection product. However, its life is limited when applied to articles such as carpets. For long term microbial and odor control, application of acidic agents such as lactic or benzoic acid, after cleaning of the article is completed, is very effective. Zinc compounds such as zinc oxide, zinc carbonate, zinc lactate, or zinc benzoate are also useful in long term odor and microbial control after the article has been cleaned. These can be applied as a spray, fine aerosol, or rinse treatment. These agents are effective in preventing the unpleasant wet carpet smell as the article is drying. This smell is usually generated by microbial activity.

Product Storage

The preferred method of storage is in a cool, dark area and in vented containers.

Product Delivery

Fine aerosol, spray, or liquid. Vented containers, such as vented spray bottles, are preferred.

What is claimed is:

1. A method of cleaning an article comprising (a) contacting said article with a composition comprising hydrogen peroxide and tri-potassium phosphate; and (b) applying an agent selected from the group consisting of lactic acid, benzoic acid, zinc oxide, zinc carbonate, zinc lactate and zinc benzoate to the article after cleaning the article with said composition.

2. A method according to claim 1 wherein the article is a carpet.

* * * * *